US005503156A

United States Patent [19]
Millar

[11] Patent Number: 5,503,156
[45] Date of Patent: Apr. 2, 1996

[54] NONINVASIVE PULSE TRANSDUCER FOR SIMULTANEOUSLY MEASURING PULSE PRESSURE AND VELOCITY

[75] Inventor: Huntly D. Millar, Houston, Tex.

[73] Assignee: Millar Instruments, Inc., Houston, Tex.

[21] Appl. No.: 212,172

[22] Filed: Mar. 11, 1994

[51] Int. Cl.⁶ .................. A61B 5/02; A61B 8/06
[52] U.S. Cl. .......................... 128/672; 128/690
[58] Field of Search ..................... 128/652, 672, 128/748, 687, 680, 660.02, 661.08, 689, 690, 667; 604/72; 73/727

[56] References Cited

U.S. PATENT DOCUMENTS

4,450,843  5/1984  Barney et al. ............. 128/690

FOREIGN PATENT DOCUMENTS

0330463  2/1989  European Pat. Off. ........ 128/661.08

OTHER PUBLICATIONS

Eckerle, J. S., *Tonometry, Arterial, Encyclopedia of Medical Devices and Instrumentation*, vol. 4: 2270–2276 (1988).
Lee, Bok Y., *Peripheral Vascular Noninvasive Measurements, Encyclopedia of Medical Devices and Instrumentation*, vol. 4: 2220–2238 (1988).

O'Rourke, Michael F., Kelly, Raymond, and Avolio, Alberto, *The Arterial Pulse*, Lea & Febiger, Chpt. 3; pp. 35–37; p. 202; Chpt. 13; Chpt. 14 (1992).
Nichols, Wilmer W. and O'Rourke, Michael F., *McDonald's Blood Flow in Arteries, Theoretical, Experimental and Clinical Principles*, pp. 159–162, 216–250, 405–408, 430–431, (3rd Ed. 1990).

*Primary Examiner*—Angela D. Sykes
*Assistant Examiner*—Stephen Huang
*Attorney, Agent, or Firm*—Arnold, White & Durkee

[57] ABSTRACT

A pulse transducer is disclosed having a pressure sensor for detecting pulse pressure and a velocity sensor for simultaneously detecting pulse velocity in blood vessels. The present invention allows reproduction of pulse pressure and velocity waveforms. The present invention combines a conventional applanation tonometer with a mounted velocity sensor, such as a Doppler crystal. The velocity sensor is placed proximate to the pressure sensor to allow simultaneous detection of pulse velocity, in real time, at substantially the same location as the pulse pressure measurement. The sensing direction of the velocity sensor may be at an angle with respect to the sensing direction of the pressure sensor. The present invention may be applied vertically to a vessel for proper applanation, while ultrasound, traveling across the vessel, may be used to detect a major component of the velocity. The present invention further contemplates a method of simultaneously measuring pulse velocity and pressure with a pulse transducer.

21 Claims, 5 Drawing Sheets

NONINVASIVE PULSE TRANSDUCER FOR SIMULTANEOUSLY MEASURING PULSE PRESSURE AND VELOCITY

BACKGROUND OF THE INVENTION

The present invention relates to pulse transducers for measuring pulse pressure and velocity in blood vessels. In particular, the present invention relates to applanation tonometers for noninvasively detecting and reproducing pulse pressure waveforms in peripheral vessels and to velocity sensors for noninvasively detecting and reproducing pulse velocity waveforms.

Existing devices provide pulse pressure detectors for noninvasively measuring pulse pressure waveforms in peripheral vessels. The ideal device is an applanation tonometer which flattens the vessel wall and, by negating the effect of the wall tension, measures the internal pulse pressure within the vessel. The tonometer provides continuous measurement throughout the heart's pumping cycle. In actual use, a tonometer faces a certain amount of tissue between the vessel and the sensor. While accurate internal pressures are not obtained, an accurate waveform reproduction of internal pressures is obtained. Because it is noninvasive, the tonometer can provide accurate, continuous blood pressure measurement with negligible risk. Further, tonometry in combination with Doppler flow techniques make possible noninvasive determination of arterial impedance. The use of tonometers is discussed in J. S. Eckerle, "Arterial Tonometry," *Encyclopedia of Medical Devices and Instrumentation,* pages 2770–2776 (New York 1988); and Michael F. O'Rourke, *The Arterial Pulse,* pages 25–34 (New York 1992).

In general, an arterial system behaves somewhat like a mechanical plumbing system. Pressure pulses travel down tubes, bounce off obstructions and send reverberations and counterpulses back up the tubes. An applanation tonometer detects analogous pressure pulses in blood vessels. By existing computer analysis techniques, the waveforms are sorted out into their original components to obtain resultant waveforms, including all the complex reflections. The resulting waveforms give information concerning the stiffness of the blood vessel measured, the age of the patient, obstructions in the vessel, and, in many cases, the condition of the heart itself. Applanation tonometry, because it is noninvasive, provides many advantages over invasive techniques. Noninvasive techniques are much less costly and avoid problems such as arterial trauma and infection.

Pulse velocity measurements are also important in studying the dynamics of blood vessels. Velocity waveforms, like pressure waveforms, will yield information useful in determining characteristics of vessels. Existing noninvasive devices have used velocity sensors, such as Doppler crystal probes, to insonate a vessel for pulse detection. By measuring the reflected ultrasound waves, pulse velocity in a vessel may be noninvasively measured. These measurements are generally not quantified and are used merely to detect the presence of a pulse. For example, a pulse velocity detector may be used to follow a vessel down an injured leg in order to detect the spot of no flow where possible surgery may be required. The use of ultrasound for noninvasive measurements is discussed in Bok Y. Lee, "Peripheral Vascular Noninvasive Measurements," *Encyclopedia of Medical Devices and Instrumentation,* pages 2220–2224 (New York 1988).

Pressure waveform measurements and simultaneous velocity waveform measurements are also useful in analyzing the condition of vessels. For example, simultaneously recorded pressure/velocity relationships may also be utilized to express vascular impedance. Impedance gives valuable information on the presence and intensity of wave reflections and permits a pressure wave to be separated into a forward traveling wave and a backward traveling wave. Analysis of pressure waveforms and velocity waveforms have been conducted using invasive techniques.

What is needed is a noninvasive device that will allow the study of hemodynamics of blood vessels. In particular, there is a need for a noninvasive device that will allow simultaneous measurement of pulse velocity and pressure in blood vessels. Noninvasive measurement techniques, to the extent they yield significant information, are preferable over invasive measurements techniques. Although existing catheters provide simultaneous velocity and pressure measurements, such catheters are highly invasive. Existing noninvasive devices do not provide for simultaneous measurement of pressure and velocity of blood flow at substantially the same location in a single vessel. Such simultaneous measurements would provide useful information in analyzing vessels. No noninvasive device has been developed to meet this need.

SUMMARY OF THE INVENTION

The problems outlined above are addressed by the device and method of the present invention. The present invention combines an applanation tonometer with a mounted velocity sensor, such as a Doppler crystal. The addition of the velocity sensor in a applanation tonometer provides a surprisingly effective and accurate device for making noninvasive simultaneous measurements of pulse pressure and velocity waveforms in blood vessels. The velocity sensor is placed proximate to the pressure sensor to allow simultaneous determination of pulse velocity, in real time, at substantially the same location as the pulse pressure measurement. The sensing direction of the velocity sensor is at an angle with respect to the sensing direction of the pressure sensor. A device according to the present invention may be applied vertically to a vessel for proper applanation, while ultrasound, traveling across the vessel, may be used to detect a major component of the velocity. Accurate pulse velocity and pressure waveforms may be detected and reproduced.

The present invention contemplates a noninvasive pulse transducer including a sensor holding assembly, a pressure sensor coupled to said sensor holding assembly, and a velocity sensor coupled to said sensor holding assembly proximate to said pressure sensor. Said velocity and pressure sensors allow simultaneous detection of pulse pressure and velocity. Further embodiments of the present invention allow detection of pulse pressure and velocity at substantially the same point in a blood vessel and reproduction of pressure and velocity waveforms. In a further embodiment, the pressure sensor has a pressure sensing direction along a first axis, and the velocity sensor has a velocity sensing direction along a second axis, the second axis being at an angle with respect to said first axis.

The present invention further contemplates a method for noninvasively detecting pulse pressure and velocity in a blood vessel. This method includes providing a pulse transducer having a pressure sensor and a velocity sensor, applying said pulse transducer to a vessel to obtain measuring contact with said vessel, and simultaneously detecting pulse velocity and pressure in said vessel. Further embodiments provide for simultaneously detecting pulse velocity and pressure at substantially the same point in the vessel and reproducing pulse velocity and pressure waveforms.

The present invention further contemplates a method of noninvasively evaluating pulse transmission through blood vessels. This method includes providing at least two pulse transducers each having a pressure sensor and a velocity sensor, applying said pulse transducers to different locations on vessels to obtain measuring contact with said vessels, simultaneously detecting and reproducing pulse velocity and pressure waveforms at substantially the same point within said vessels at said different locations to produce a set of pulse velocity and pressure measurements for each location, and comparing said sets of pulse velocity and pressure waveforms to evaluate pulse transmission between said locations on said vessels. The locations may be at a single location on two different vessels, such as the carotid and radial arteries, or may be at two locations on a single peripheral vessel, such as the radial artery.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and can be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION OF THE PREFERRED EMBODIMENTS

Figure 1:
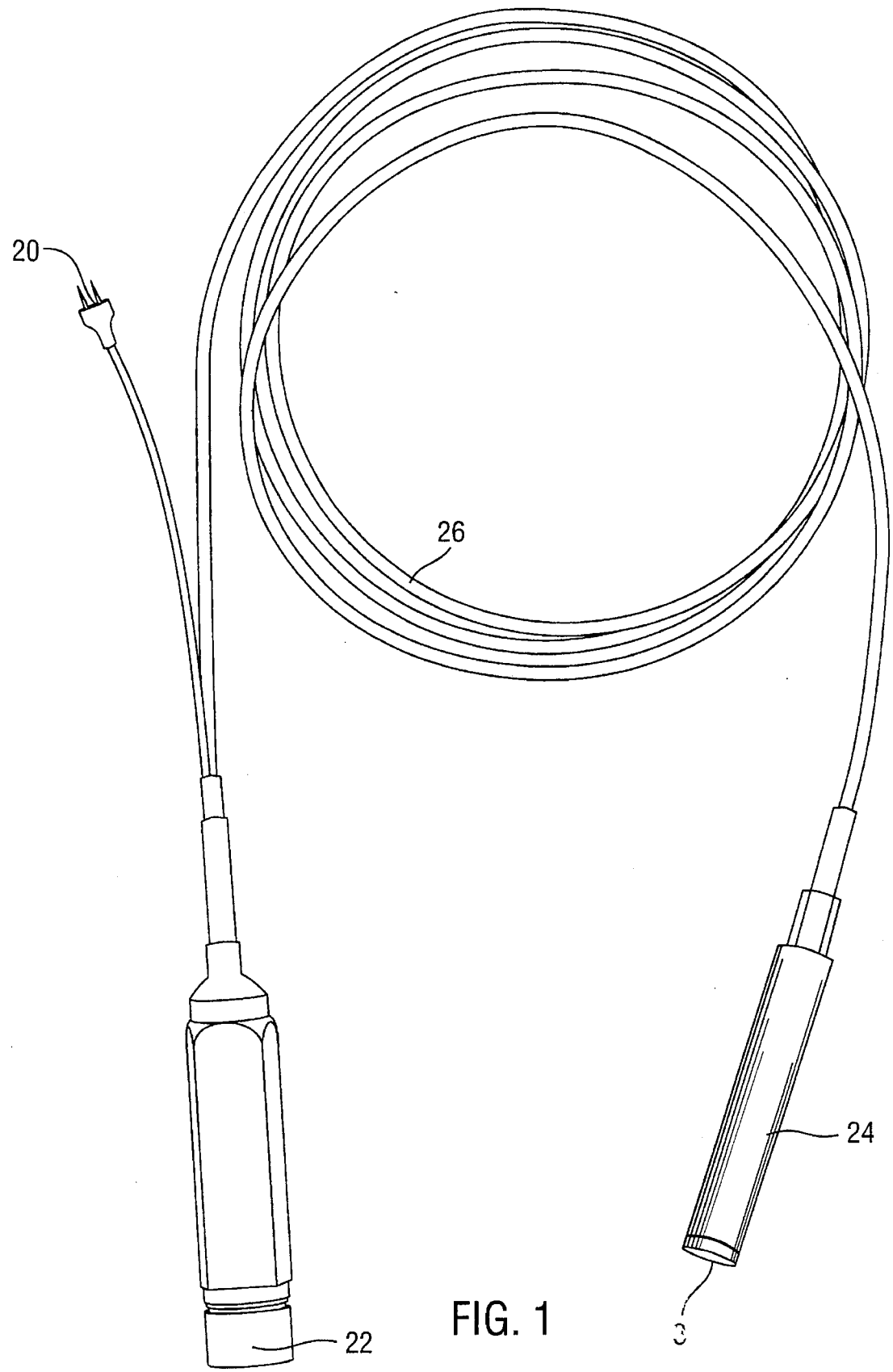
FIG. 1 illustrates an embodiment of the present invention.

Turning now to the drawings, FIG. 1 illustrates a pulse transducer according to the present invention. Sensor holding assembly 3 is attached to probe 24 at its tip. Sensor holding assembly 3 includes a pressure sensor and a velocity sensor. The pressure sensor is connected to pressure sensor connector 22 through cable 26. Pressure sensor connector 22 connects to a standard medical pressure monitor, such as the Hewlett-Packard Patient Monitor, model number 78353A, which is available from Hewlett-Packard in Waltham, Mass. Velocity sensor 9 is connected to velocity sensor connector 20 through cable 26. Velocity sensor connector 20 connects to a standard commercial velocimeter, such as the Millar Velocimeter, model MDV-20, available from Millar Instruments, Inc., in Houston, Tex. The use of a standard medical pressure monitor and the use of a standard velocimeter are known to one of skill in the art. Without the velocity sensor, a pulse transducer according to the present invention is similar to commercially available applanation tonometer, such as Millar Pulse Pressure Transducer, model SPT-301, from Millar Instruments, Inc., in Houston, Tex.

Figure 2:
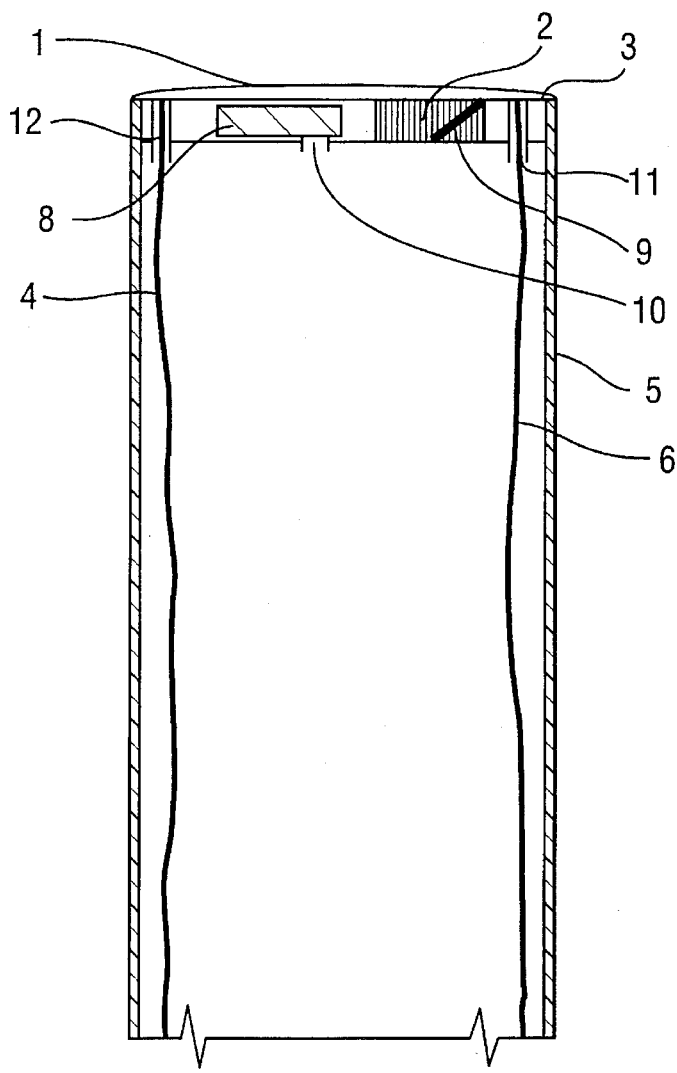
FIG. 2 illustrates a cross-section view of the measuring end of an embodiment of the present invention.

FIG. 2 illustrates a cross-sectional view of the measuring end of an embodiment of the present invention. Probe 24 may be of any desirable form. For example, probe 24 may include stainless steel housing 5, which provides support for sensor holding assembly 3. Sensor holding assembly 3 provides structure to support pressure sensor 8 and velocity sensor 9. The length of stainless steel housing 5 is not critical but may be chosen to provide ease of manipulation. The diameter of stainless steel housing 5 may be chosen to match the diameter of sensor holding assembly 3. For example, dimensions for stainless steel housing 5 may be 2.5 inches in length and 0.25 inch in diameter.

Pressure sensor 8 provides measurements of pulse pressure in a blood vessel. Pressure sensor 8 has a sensing side and a reference side. The sensing side is directed outwardly from the end of steel housing 5. The reference side is in communication with atmospheric pressure through vent hole 10. Vent hole 10 provides access to atmospheric pressure, for example, through cable 26. Lead 4 provides communication between pressure sensor 8 and a conventional medical pressure monitor. Pressure sensor 8 may be a pressure sensor such as those in commercially available applanation tonometers. Such pressure sensors, or blood pressure transducers, are known to those skilled in the art and are available from such companies as Foxboro and Lucas Novasensor in San Jose, Calif. In particular, pressure sensor 8 may be a silicon pressure sensor chip with a thin diaphragm and two strain gauges. Lead 4 may be three wires coupled to pressure sensor 8.

Velocity sensor 9 provides measurements of pulse velocity in blood vessels. Velocity sensor 9 has a measuring side directed at an angle with respect to the sensing direction of pressure sensor 8. Lead 6 provides communication between velocity sensor 9 and a standard commercially available velocimeter. Velocity sensor 9 may be a pulsed Doppler pressure sensor. Such velocity sensors are known to those skilled in the art. Pulsed Doppler sensors utilize a single Doppler crystal. In particular, the Doppler crystal may be Model G1195 Doppler crystal available from Piezo Electric Products, Inc., in Metuchen, N.J. The Doppler crystal acts as a transmitter when a 20 MHz pulse is applied to it and as a receiver for the ultrasound waves that are reflected back from the moving blood. The Doppler crystal is pulsed between transmitting and receiving modes at 62 kHz. Lead 6 may be two wires coupled to velocity sensor 9.

The Doppler transmission frequency of 20 MHz provides for detection of pulse velocity within a vessel that is approximately 8–10 mm from the skin surface. It should be noted that the transmission frequency may be altered to measure blood vessels at different distances from the Doppler sensor. For example, lower frequency transmissions may be used to obtain velocity measurements for arteries lying deeper beneath the skin. Therefore, lower frequency Doppler crystals, such as a 10 MHz crystal, may be utilized for measuring deeper vessels.

Figure 4:
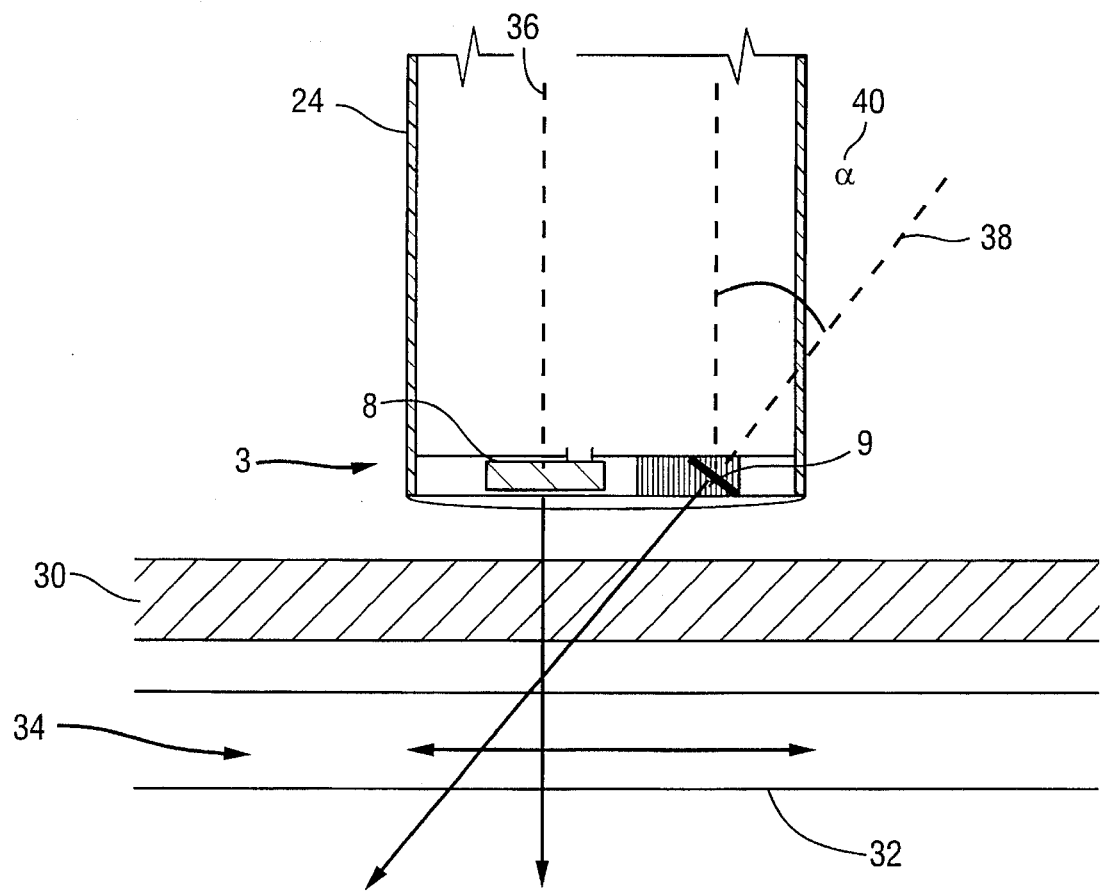
FIG. 4 illustrates the directional arrangement of pressure sensor and velocity sensor according to the present invention.

For proper simultaneous detection of pulse pressure and velocity at substantially the same location in a vessel, velocity sensor 9 may be directed at an angle to the direction of pressure sensor 8. FIG. 4 illustrates the directional arrangement of pressure sensor 8 and velocity sensor 9. To begin measurement, probe 24 is pressed against skin 30, which in turn presses against blood vessel 32. Blood flow 34 travels through blood vessel 32. Pressure sensor 8 measures pulse pressure along pressure axis 36, which is generally desired to be perpendicular to blood vessel 32. Velocity sensor 9 measures pulse velocity of blood flow 34 along velocity axis 38, which is preferably at angle 40 to pressure axis 36. Because blood flow 34 is not directly toward or away from velocity sensor 9, velocity sensor 9 will measure a component of the velocity of blood flow 34. This component will be a function of angle 40. If velocity axis 38 is parallel to pressure axis 36, velocity axis 38 would be perpendicular to blood flow 34, and no velocity would be measured. Although angle 40 may be between 0 and 90 degrees, a preferable range would be 30 to 60 degrees. A good compromise for angle 40 is 45 degrees. Further, velocity sensor 9 may be positioned with a slight separation from pressure sensor 8, so that the sound transmitted from velocity sensor 9 has a substantially unobstructed path to the vessel being measured. The direction of blood flow 34 is not significant because upstream measurements simply produce inverted measurements from downstream measurements. It should be noted that velocity axis 38 may also be pointed away from pressure axis 36 such that detection paths never cross.

Velocity sensor 9 may also be a continuous wave Doppler sensor. Such velocity sensors are known to those skilled in the art. Continuous wave Doppler sensors utilize multiple Doppler crystals. A transmitting crystal emits ultrasound. Backscattered sound is detected by a second, receiving crystal. The frequency received correlates to the pulse velocity of the measured blood vessel.

Sensor holding assembly 3 provides structure for the sensors of the present invention. Pressure sensor 8 and velocity sensor 9 are attached to sensor holding assembly 3. The only size requirement of sensor holding assembly 3 is that it is large enough to hold pressure sensor 8 and velocity sensor 9. Vent hole 10 passes through sensor holding assembly 3 and provides communication between the reference side of pressure sensor 8 and atmospheric pressure through stainless steel housing 5 and cable 26. Sensor holding assembly 3 also includes lead opening 12 for lead 4 and lead opening 11 for lead 6. Sensor holding assembly 3 also includes a cavity for pressure sensor 8 and a cavity for velocity sensor 9. Sensor holding assembly 3 may be made of any material of sufficient strength to provide support for pressure sensor 8 and velocity sensor 9. In particular, sensor holding assembly 3 may be made of filled epoxy resin that may be molded and hardened to include the above mentioned features. Sensor holding assembly 3 may be cylindrical and be ⅛ inch in length and ¼ inch in diameter.

Sensor holding assembly 3 is covered by a pressure transmitting membrane 1 to provide communication between a blood vessel and pressure sensor 8. Pressure transmitting membrane 1 insulates lead 4 from the outside surface and allows transmission of pressure to the pressure sensor diaphragm of pressure sensor 8. Pressure transmitting membrane 1 does not extend over the cavity for velocity sensor 9, which is filled with sound transmitting medium 2. Sound transmitting medium 2 fills the velocity sensor cavity and fixes the position of the velocity sensor. Pressure transmitting membrane 1 may be a silicone rubber overlay. Sound transmitting medium 2 may be clear epoxy resin. The particular compounds used are not significant as long as they allow pressure sensor 8 and velocity sensor 9 to perform properly and protect the sensors from contact with the patient.

Figure 3:
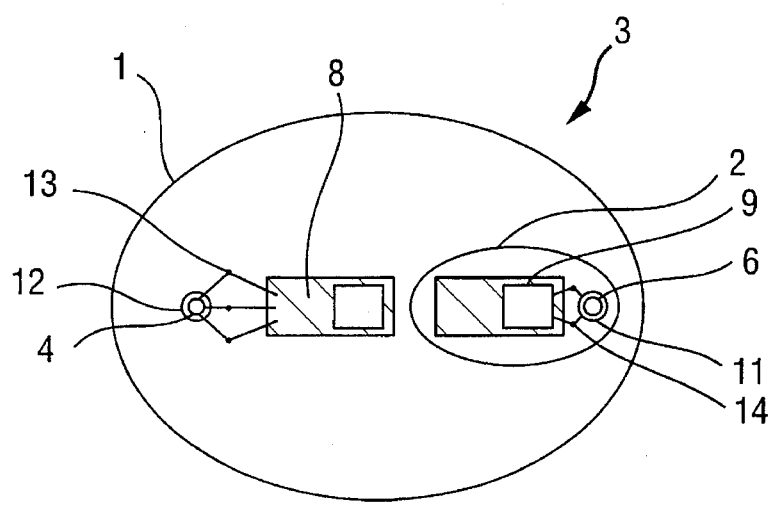
FIG. 3 illustrates a top view of the measuring tip of an embodiment of the present invention.

FIG. 3 illustrates a top view of sensor holding assembly 3. Lead 4 travels through lead opening 12 and connects to pressure sensor 8 at solder point 13. Lead 6 travels through lead opening 11 and connects to velocity sensor 9 at solder point 14. Pressure transmitting membrane 1 covers the entire face of sensor holding assembly 3, except for sound transmitting medium 2 which covers velocity sensor 9.

Figure 5:
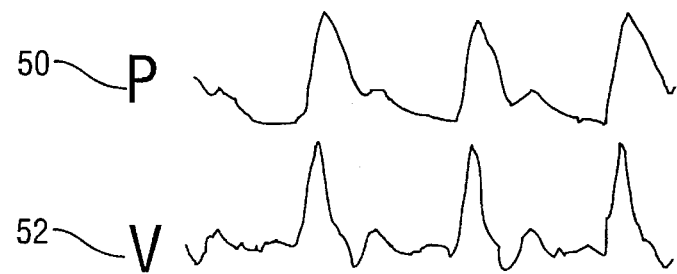
FIG. 5 illustrates the resulting waveforms produced by measurements made with the present invention.

FIG. 5 illustrates the resulting waveforms obtained utilizing measurements made by the present invention. Pressure sensor 8 provides information representative of pulse pressure within the measured vessel to a standard medical pressure monitor. The pressure monitor analyzes the information from pressure sensor 8 and converts that information into a representative waveform. The pulse pressure waveform is represented by waveform 50. Velocity sensor 9 provides information representative of pulse velocity within the measured vessel to a standard velocimeter. The velocimeter analyzes the information from velocity sensor 9 and converts that information into a representative waveform. The pulse velocity waveform is represented by waveform 52. The present invention provides measurements of pulse pressure, pulse velocity, relative blood flow, and changes in blood flow. The present invention does not provide absolute blood flow measurements, unless the dimensions of the vessel being measured are known. If the dimensions are known, blood flow may be determined from the pulse velocity measurement. Pulse velocity and pulse pressure measurements and representative waveforms are discussed in J. S. Eckerle, "Arterial Tonometry," Encyclopedia of Medical Devices and Instrumentation, pages 2770–2776 (New York 1988); Michael F. O'Rourke, "The Arterial Pulse," pages 25–34 (New York 1992); and Bok Y. Lee, "Peripheral Vascular Noninvasive Measurements," Encyclopedia of Medical Devices and Instrumentation, pages 2220–2224 (New York 1988). These references are hereby incorporated by reference in their entirety.

Figure 6A:
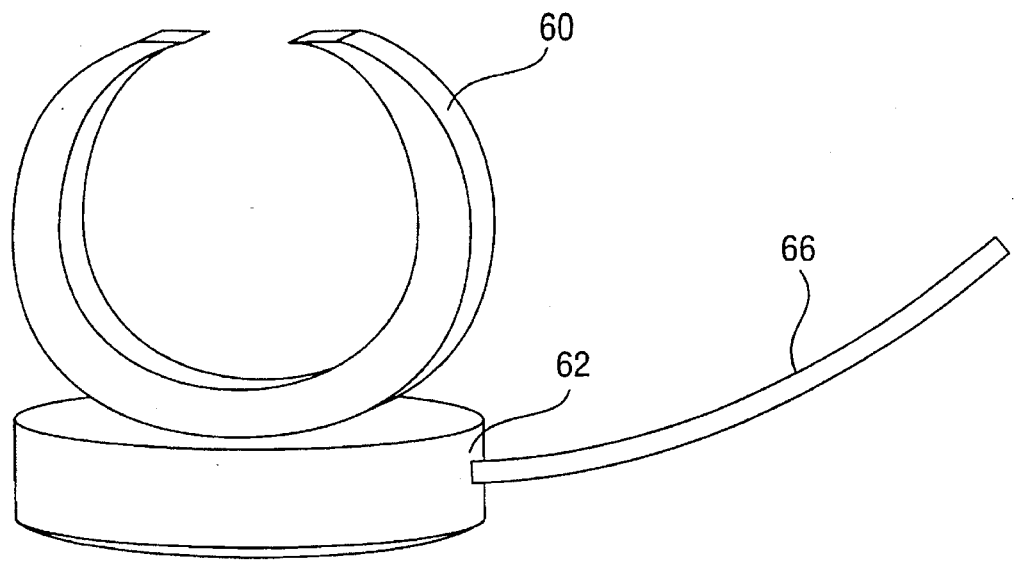
FIG. 6A illustrates a finger pulse transducer according to the present invention.
Figure 6B:
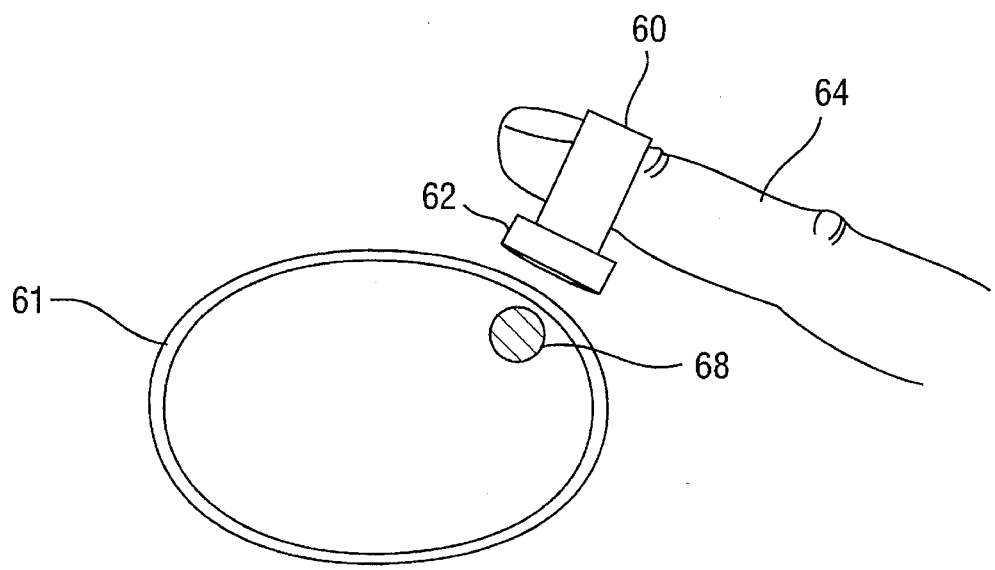
FIG. 6B illustrates a cross-sectional view of a finger pulse transducer applied to a vessel.

FIG. 6A and FIG. 6B illustrate a finger pulse transducer according to the present invention. Finger attachment 60 secures pulse transducer 62 to finger 64. Pulse transducer 62 includes a pressure sensor and a velocity sensor, as discussed above, that are in communication with monitoring devices through cable 66. The pressure sensor and the velocity sensor are directed away from finger 64. With pressure applied by finger 64, pulse transducer 62 may used to measure pulse velocity and pressure in blood vessels, such as radial artery 68 in wrist 61. Finger attachment 60 may be made of silicone rubber in the shape of an open ring. Similar devices may be constructed for attachment to other instruments or body parts of the user.

Figure 7A:
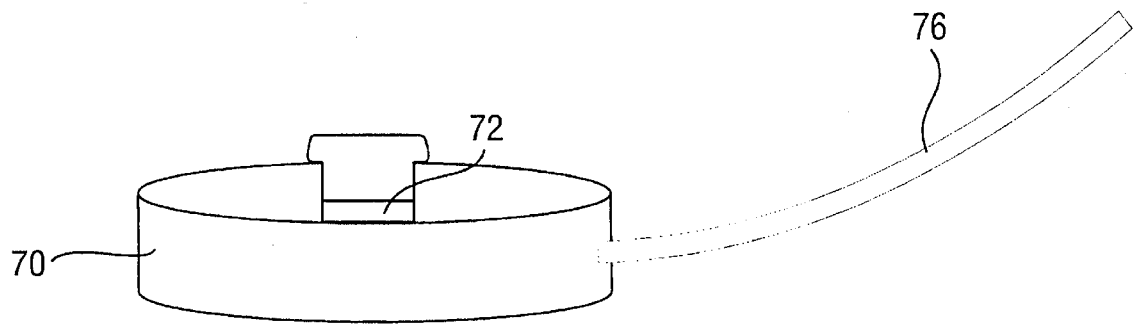
FIG. 7A illustrates a wrist strap pulse transducer according to the present invention.
Figure 7B:
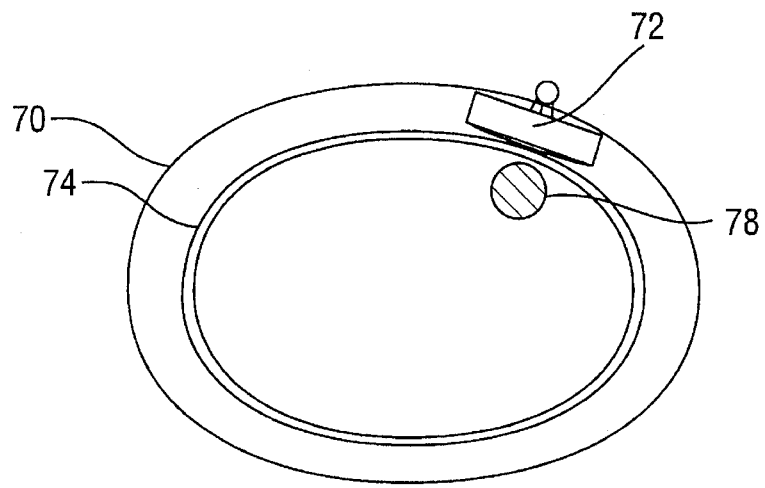
FIG. 7B illustrates a cross-sectional view of a wrist strap pulse transducer applied to a vessel.

FIG. 7A and FIG. 7B illustrate a wrist pulse transducer according to the present invention. Wrist strap 70 secures pulse transducer 72 to wrist 74. Pulse transducer 72 includes a pressure sensor and a velocity sensor, as discussed above, that are in communication with monitoring devices through cable 76. The pressure sensor and the velocity sensor are directed toward wrist 74. With pressure applied by wrist strap 70, pulse transducer 72 may be used to measure pulse velocity and pressure in radial artery 78. Wrist strap 70 may be made of elastic rubber and may be adjustable. Similar devices may be constructed for measuring pulse information in other peripheral arteries.

In operation, a pulse transducer according to the present invention is held above the vessel to be measured. The pulse transducer is applied to the blood vessel to be measured noninvasively (e.g. by pressing down the skin above the vessel). In applying the pulse transducer, it may be necessary to place a drop of water on the skin to aid in conduction of ultrasound. The pulse transducer is adjusted until a pulse is indicated by information from the pressure sensor or the velocity sensor. A line mark, or other indication, may be provided to show the measuring direction of the velocity sensor so that it may be lined up with the downstream or upstream direction of the vessel being measured. Blood vessels that may be measured by a pulse transducer according to the present invention include: peripheral vessels such as carotid artery, radial artery, femoral artery, and brachial artery; veins; or any other accessible blood vessel. The close proximity of the pressure sensor and the velocity sensor allow simultaneous measurement of pulse velocity and pressure at substantially the same point in the vessel being measured.

A standard pressure monitor will provide an output when the pressure sensor picks up a pulse. A standard velocimeter will produce an output when the velocity sensor picks up a pulse. A standard velocimeter will also produce an audible output dependent upon the rate of change in measured pulse velocity of the blood vessel. This audio output may be used to locate the pulse in a vessel to be measured. The audible output of velocity change will be readily identifiable by the user when good positioning of the sensors of the present invention has occurred. The velocity sensor allows this audible output to be used where pulse pressure information from the pressure sensor does not clearly identify good placement of the pulse transducer. For example, in finding good placement in measuring the brachial artery, audible output using the velocity sensor is clearly heard when good positioning has occurred. Only small signal information is gained from the pressure sensor.

Multiple devices according to the present invention may also be used to evaluate the condition of the vascular system. For example, measurements may be made simultaneously at two different points with two pulse transducers according to the present invention to evaluate pulse transmission. For example, simultaneous measurements may be made at the carotid artery and at the radial artery or femoral artery to evaluate pulse transmission from the central pulse to the periphery. Simultaneous measurements may be made on both sides of the body to show whether circulation is impaired in one side as compared to the other. Simultaneous measurements may also be made at two places along a single vessel to determine pulse transit time in that vessel. Further a single pulse transducer may be used to measure pulse velocity and pressure at different locations on the same or different vessels, and the resulting velocity and pressure measurements may be analyzed.

It should be noted a pulse transducer according to the present invention may be used to obtain other measurements, if desired, rather than detecting and reproducing pressure and velocity waveforms. Further a pulse transducer according to the present invention may be used to measure pulse pressure and velocity of vessels exposed during surgery. In particular, the present invention may be useful in surgical graft procedures to determine if grafting has been successful. The present invention may be useful in finding an obstruction in a vessel during a surgical procedure and in determining if the procedure utilized has fixed the problem. The present invention may also be used in evaluating or monitory a patient's progress after surgical procedures in post-operative follow-ups, for example, after a graft operation. Measurements may be made during surgery or immediately upon closing. Later monitoring measurements may be compared to earlier measurements to determine if problematic changes have occurred in the vascular system.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A noninvasive pulse transducer comprising:

a sensor holding assembly;

a pressure sensor coupled to said sensor holding assembly, said pressure sensor having a pressure sensing direction along a first axis; and a velocity sensor coupled to said sensor holding assembly proximate to said pressure sensor, said velocity sensor having a velocity sensing direction along a second axis, said velocity sensing direction being directed toward said pressure sensing direction and said second axis being at an angle with respect to said first axis;

such that said pressure sensor and said velocity sensor allow simultaneous detection of pulse pressure and velocity in a blood vessel.

2. The noninvasive pulse transducer of claim 1, wherein said angle of said second axis with respect to said first axis is in the range from 30 to 60 degrees.

3. The noninvasive pulse transducer of claim 1, wherein said angle of said second axis with respect to said first axis is 45 degrees.

4. The noninvasive pulse transducer of claim 1, wherein said velocity sensor is a pulsed Doppler velocity sensor.

5. The noninvasive pulse transducer of claim 1, wherein said velocity sensor is a continuous wave Doppler velocity sensor.

6. The noninvasive pulse transducer of claim 1, wherein said pressure sensor is a silicon pressure sensor chip.

7. The noninvasive pulse transducer of claim 1, wherein said simultaneous detection is at substantially a same point in said blood vessel.

8. The noninvasive pulse transducer of claim 1, further comprising:

a velocity sensor connector in communication with said velocity sensor and adapted to connect to a standard medical velocimeter; and a pressure sensor connector in communication with said pressure sensor and adapted to connect to a standard medical pressure monitor.

9. The noninvasive pulse transducer of claim 8, further comprising:

a probe coupled to said sensor holding assembly; and a cable coupled to said probe at a first end and to said pressure sensor connector and to said velocity sensor connector at a second end.

10. The noninvasive pulse transducer of claim 1, further comprising:

an attachment assembly coupled to said sensor holding assembly.

11. The noninvasive pulse transducer of claim 10, wherein said attachment assembly comprises:

a silicon rubber open ring coupled to said sensor holding assembly, said ring adapted to attach to a finger and said sensing directions of said pressure and velocity sensors being outward from said finger.

12. The noninvasive pulse traducer of claim 10, wherein said attachment assembly comprises:

an adjustable elastic band coupled to said sensor holding assembly, said band adapted to attach to a wrist and said sensing directions of said pressure sensor and said velocity sensor being toward said wrist.

13. A method for noninvasively determining pulse, pressure and velocity in a blood vessel, comprising:

providing a pulse transducer having a sensor holding assembly including a pressure sensor and a velocity sensor, said pressure sensor having a pressure sensing direction along a first axis and said velocity sensor having a velocity sensing direction along a second axis, said velocity sensing direction being directed toward said pressure sensing direction and said second axis being at an angle with respect to said first axis;

applying said pulse transducer to a vessel to obtain measuring contact with said vessel; and simultaneously determining pulse velocity and pressure in said vessel.

14. The method of claim 13, wherein said determining step comprises:

simultaneously determining pulse velocity and pressure in said vessel at substantially a same point in said vessel.

15. The method of claim 13, further comprising:

reproducing pulse velocity and pressure wave forms from said determination of pulse velocity and pressure.

16. The method of claim 13, wherein said applying step comprises:

applying said pulse transducer to a peripheral artery or vein.

17. The method of claim 14, wherein said applying step comprises:

applying said pulse transducer to an artery or vein exposed during surgery.

18. The method of claim 13, further comprising:

applying said pulse transducer to a second vessel to obtain measuring contact with said second vessel;

simultaneously determining pulse velocity and pressure in said second vessel at substantially a same point in said second vessel; and comparing said pulse velocity and pressure measurements from said vessels.

19. A method of noninvasively evaluating pulse transmission through blood vessels, comprising:

providing at least two pulse transducers each having a sensor holding assembly including a pressure sensor and a velocity sensor, said pressure sensor having a pressure sensing direction along a first axis and said velocity sensor having a velocity sensing direction along a second axis, said velocity sensing direction being directed toward said pressure sensing direction and said second axis being at an angle with respect to said first axis;

applying said pulse transducers to different locations on vessels to obtain measuring contact with said vessel;

simultaneously determining and reproducing pulse velocity and pressure wave forms at substantially a same point in said vessels at said different locations to produce a set of pulse velocity and pressure wave forms for each location; and comparing said sets of pulse velocity and pressure wave forms to evaluate pulse transmission between said locations on said vessels.

20. The method of claim 19, wherein said applying step comprises:

applying a first pulse transducer to a location on a first vessel and applying a second pulse traducer to a location on a second vessel.

21. The method of claim 19, wherein said applying step comprises:

applying a first pulse transducer to a first location on a vessel and applying a second pulse transducer to a second location on said vessel.

* * * * *

UNITED STATES PATENT AND TRADEMARK OFFICE
CERTIFICATE OF CORRECTION

PATENT NO.   :   5,503,156

DATED        :   April-2, 1996

INVENTOR(S)  :   Huntly D. Millar

It is certified that error appears in the above-identified patent and that said Letters Patent is hereby corrected as shown below:

In claim 12, column 9, line 3, delete "traducer" and insert --transducer--.

In claim 20, column 10, line 33, delete "traducer" and insert --transducer--.

Signed and Sealed this

Twenty-fifth Day of June, 1996

Attest:

BRUCE LEHMAN

Attesting Officer    Commissioner of Patents and Trademarks